United States Patent
Walter et al.

(10) Patent No.: US 7,145,027 B2
(45) Date of Patent: Dec. 5, 2006

(54) METHOD FOR PRODUCING CHLOROTRIS(TRIPHENYLPHOSPHINE) RHODIUM (I)

(75) Inventors: Richard Walter, Alzenau (DE); Horst Meyer, Altenstadt (DE)

(73) Assignee: W.C. Heraeus GmbH & Co. KG, Hanau (DE)

( * ) Notice: Subject to any disclaimer, the term of this patent is extended or adjusted under 35 U.S.C. 154(b) by 0 days.

(21) Appl. No.: 10/526,912

(22) PCT Filed: Jul. 8, 2003

(86) PCT No.: PCT/EP03/07292

§ 371 (c)(1),
(2), (4) Date: Oct. 18, 2005

(87) PCT Pub. No.: WO2005/005448

PCT Pub. Date: Jan. 20, 2005

(65) Prior Publication Data

US 2006/0058543 A1    Mar. 16, 2006

(51) Int. Cl.
*C07F 15/00* (2006.01)
*B01J 31/00* (2006.01)

(52) U.S. Cl. .................................. 556/21

(58) Field of Classification Search .......... 556/21
See application file for complete search history.

(56) References Cited

OTHER PUBLICATIONS

Osborn, J.A. et al., "Inorganic Syntheses", pp. 67-71 (1967), McGraw Hill Book Co.
Osborn, J.A. et al., "Inorganic Syntheses", pp. 77-79, (1990), McGraw Hill Book Co.
Suggs, J.W. et al., "Synthesis, structure and ligand-promoted reductive elimination in an acylrhodium ethyl complex", Organometallics (1985), 4, pp. 1101-1107.

*Primary Examiner*—Porfirio Nazario-Gonzalez
(74) *Attorney, Agent, or Firm*—Norris McLaughlin & Marcus, P.A.

(57) ABSTRACT

A process is described for the manufacture of chlorotris (triphenylphosphine)-rhodium(1) by means of causing a reaction of $RhCl_3$ solution with triphenylphosphin in mixtures of C2–C5 alcohols with water
subsequently cooling down and filtering the crystalline precipitate obtained characterized in that the mixture of the reactants is handled in such a way that
B is warmed up to 75° C., and
C is maintained at 80 to 110° C.

The technique leads to improvements in the yield and quality of the crystals obtained.

8 Claims, No Drawings

METHOD FOR PRODUCING CHLOROTRIS(TRIPHENYLPHOSPHINE) RHODIUM (I)

This is a 371 of PCT/EP03/07292 filed Jul. 8, 2003.

The invention has to do with a technique for the manufacture of chlorotris(triphenylphosphine)rhodium(1). This compound became known as "Wilkinson's Catalyst" and is utilized in numerous industrial processes, mainly hydrogenations and hydroformylations. The most familiar method for the manufacture of them stems from Sir Geoffrey Wilkinson and has found its way into the standard reference work "Inorganic Syntheses" [Inorg. Synth 10, 67 (1967) and identically Inorg. Synth 28, 77 (1990)]. According to this technique $RhCl_3$-hydrate is made to react with excess triphenylphosphine in ethanol and the compound is obtained in a yield of 88% relating to the rhodium used.

It has now been discovered that the technique can be decisively improved both in terms of the product's yield as well as in terms of quality. Surprisingly during the reaction temperature control directly and demonstrably impacts the product's quality.

BACKGROUND OF THE INVENTION

With large-scale manufacture of Wilkinson's Catalyst the determining factor is that a crystalline product be obtained that is well filterable. In this respect crystals too small are not useful because they clog filtering devices, such as filters, Filter funnels or frits, or the filters cannot retain the crystals. It has been discovered that the size of the crystal is surprisingly adjustable by means of temperature and solvents.

SUMMARY OF THE INVENTION

The invention thus has to do with a technique for the manufacture of chlorotris(tri-phenylphosphine)rhodium(1) by reaction of a $RhCl_3$ solution with triphenylphosphin in mixtures of a $C_2$–$C_5$ alcohol with water, subsequent cooling and filtering of the crystalline precipitate obtained whereby the mixture of the reactants is handled in such a way that A in an initial stage is heated up to about 30° C.,
B later in a second stage is heated up from 30 to about 75° C.,
C is maintained at 80 to 110° C.

In so doing Stage A can be eliminated if the mixture is already 30° C. warm or warmer (cf. Embodiment 1). Stages A and B can even merge if for somewhat more than a time period of 3/2 to several hours it is heated up from room temperature (cf. Embodiment 3). As can be seen from the embodiments the temperature indication of "about 30° C." is relating to a temperature range of 25 to 35° C. Also the indication of "about 75° C." refers to a temperature range that lies between 68 and 79° C. and in which with the inventive technique the point of change into a deep dark red solution normally lies, showing the reaction has taken place completely. Further, with the use of ethanol as a solvent the lower temperature limit at step C is to be lowered to 78° C.

Preferably the duration of the individual stages amounts to: A about ½–1 h, B about 1–4 h and C about ½–1 h. Here the limits are to be taken loosely, that means, e.g., +/–10 minutes with a half hour and +/–30 minutes with 4 hours. However an effort is made for economic reasons not to design the duration of the stages too long.

Particularly beneficial is a technique for the manufacture of chlorotris(tri-phenylphosphine)rhodium(1), by which a solution of $RhCl_3$ is manufactured in water or a $RhCl_3$ solution is prepared from a recycling process.
the solution is combined with a $C_2$–$C_5$-alcohol combined, preferably isopropanol, if need be in a protective inert gas and/or under cooling (e.g. in an ice bath),
triphenylphosphin is added in excess, if need be as alcohol solution or suspension, if need be again under cooling.
A the mixture or suspension obtained is heated up in an initial stage from about 5 to 20 to about 30° C.,
B later in a second stage is heated up from about 30 up to about 75° C.,
C maintained at 80 to 110 ° C. or, if need be, boiled under reflux,
the solution obtained is cooled down,
the crystals precipitated out are filtered, washed with alcohol and/or water and/or petroleum ether and subsequently dried.

Preferably at Step B the heat-up is done slowly in such a way that the solution's color change to dark red takes place at the highest possible temperature, by preference at about 75° C. This change indicates the reaction to chlorotris (triphenylphosphine)rhodium(1) that later is obtained as dark red crystals. On fast heat-up of the suspension in Step B the dark red color change already occurs at about 60° C. Later upon cool down such small crystals arise that the filtration appliances, such as frits, clog or the filter is not able to retain the crystals. If the temperature is controlled in such way that at first it is heated up for some time (with starting points in the 100 g range ½ h) from room temperature (18 to 20° C.) to about 30° C., then in an additional phase about 3 h. long is heated up from about 30 to 75° C., the color change first takes place at about 75° C. The resulting crystals are demonstrably adequate in size to be smoothly filtered and also meet catalyst users' requirements and specifications.

In a preferred embodiment of the technique the $RhCl_3$ is used in the form of an aqueous solution from a recycling process. Surprisingly this has an impact on the quality of the crystals obtained. At the same time the determining factor appears to be the role of water. Tripheylphosphin dissolves in isopropanol but is almost insoluble in water. By the thinning effect upon addition of about a 10% aqueous $RhCl_3$ solution the solubility of tripheylphosphin is reduced. This is represented in Embodiment 3, according to which a good yield of well filterable, specification-adjusted crystals is manufactured.

Alternatively thereto it can prove to be advantageous not to dissolve the triphenylphosphin in alcohol completely, but rather to use it as an alcoholic suspension. Triphenylphosphin does not dissolve in particular at low temperatures completely right away, but rather first starts dissolving slowly with rising temperature and is only then available for the reaction with $RhCl_3$. According to this effect the mole ratio between $RhCl_3$ and triphenylphosphin is different from the quantities introduced, and even here the crystal size is again surprisingly favorably impacted by the initial lack of triphenylphosphin.

The invention thus also has to do with a technique for the manufacture of cholotris(triphenylphosphine)rhodium(I), with which a $RhCl_3$ solution is manufactured in water or a $RhCl_3$ solution is prepared from a recycling process,
isopropanol is produced under an inert protective gas,
the $RhCl_3$ solution is added,
triphenylphosphin is added in excess as an alcoholic suspension, A the suspension obtained in an initial stage is heated up from about 20 to about 25 to 30° C., B further in a second stage is heated up from about 25 to 30 to about 75° C., C is boiled under reflux at 80 to 110° C., the solution obtained is cooled down, the crystals precipitated out are filtered, washed with alcohol and/or water and/or petroleum ether and subsequently dried.

An advantage of the embodiment of the technique is that the overall synthesis can transpire within a single day if, as in Embodiment 4, the reaction is started at room temperature, without preliminary cooling down of the solvent. This in practice proves to be a substantial economic advantage.

Even with the processing it has proven to be advantageous after Stage C actively to cool down the solution. Surprisingly this does not have any unfavorable impact on the crystal size and provides a great advantage by the saving of time in relation to the energy expended for cooling down.

Furthermore, it is possible to achieve an improved space-time yield by limiting the solvent quantity, as described in Example 5. With this procedure smaller crystals that may potentially arise can be filtered by means of a pressure filter so that with production of larger quantities overall a very economical technique results.

Furthermore, the crystalline product's drying process can be tweaked to the effect that washing can be done with isopropanol and if need be petroleum benzine. Thus on an industrial scale drying times of only a day are possible.

The following examples serve as illustration of the invention without limiting it. Yields are given in % relating to rhodium used.

EXAMPLES

Comparative Example: State of the Art, Wilkinson's Rule

Synthesis according to Inorg. Synth 10, 67 (1967) and identically Inorg. Synth 28, 77 (1990)

In a 500 ml round-bottomed flask with gas intake pipe, reflux condenser and gas outtake 2 g rhodium(III)-chloride-trihydrate are dissolved in 70 ml ethanol. A solution of 12 g triphenylphosphin freshly recrystallized from EtOH is added in 350 ml hot ethanol and the flask is rinsed with nitrogen. The solution is boiled at reflux for two hours and the crystalline product is filtered out of the hot solution on a frit. After washing with small portions of 50 ml water-free ethanol 6.25 g is obtained (yield: 88% relating to Rh).

Example 1

Wilkinson's Rule with Inventive Temperature Control Stage B and C

Apparatuses 1 and 2: Round-bottomed flask with gas intake, reflux cooler and gas outtake.

In apparatus 2, 24 g (0.0916 mole) triphenyphosphin under argon are produced and dissolved in 700 ml ethanol. At 40° C. the entire tripheylphosphin has already dissolved.

In apparatus 1 in the meantime, 4 g (0.0158 mole) $RhCl_3$ hydrate is produced and suspended in 140 ml ethanol. To the reddish brown suspension is now added under argon intake flow the triphenylphosphin solution warmed to 40° C. A deep red solution arises with a temperature of 36° C. The solution is now slowly heated to simmering.

| Temperature: | Processing Time: | Observation: |
|---|---|---|
| 36–62° C. | 55 min | orange suspension |
| 62–67° C. | 25 min | suspension becomes gradually darker and changes colors through brown to wine red |
| 67° C. | | reaction occurred; a dark ruby-colored suspension has arisen (change point) |
| 67–79° C. | 70 min | dark ruby-colored suspension |
| 79–80° C. | | start simmering; suspension is boiled 2 h on reflux |

The suspension obtained is cooled down by means of an ice bed to 20° C. and subsequently filtered through a G3 frit. The ruby-colored product is rewashed on the frit 2× with 50 ml ethanol each and dried in the vacuum of membrane pumps. 14,549 g of ruby-colored solid were obtained. The calculated yield amounts to 99.2%.

Example 2

4 g Rh (0.0389 mole) in form of an aqueous $RhCl_3$ solution with 23% rhodium content are dissolved under argon in 490 ml isopropanol in a round-bottomed flask with gas intake and outtake cooler and cooled down to 5° C. by means an ice bath.

With this temperature under stirring 50 g (0.191 mole) triphenylphosphin is added in and subsequently slowly heated up to simmering.

| Temperature: | Processing Time: | Observation: |
|---|---|---|
| 5° C. | | dark reddish brown solution with undissolved triphenylphosphin |
| 10–31° C. | 1 h | brown suspension |
| 25–70° C. | 3.25 h | orange suspension |
| 70–75° C. | 30 min | suspension becomes gradually darker and changes colors via brown to ruby-colored |
| 75° C. | | reaction occurred; a dark ruby-colored suspension has arisen (change point) |
| 75–79° C. | 15 min | ruby-colored suspension |
| 79–80° C. | | simmering starts; suspension is boiled for 1 h on reflux |

The suspension obtained is left to cool down over night without active cooling. On the following day cooling down to 10° C. by means of an ice bath takes place and subsequently filtering over a G3 frit. The product is rewashed on the frit with 235 ml isopropanol and 100 ml petroleum benzine and dried in the vacuum of membrane pumps.

35.81 g (0.0387 mole) of ruby-colored solid are obtained. The calculated yield amounts to 99.4%.

Example 3

One day prior to the actual synthesis 4 g Rh (0.0389 mole) in form of an $RhCl_3$ hydrate (Rh content 40.7%) is dissolved in 26 ml of totally desalinated water overnight. In a round-bottomed flask with gas intake and outtake cooler as well as reflux cooler 490 ml isopropanol are produced under argon. The $RhCl_3$ solution is added in. Then 50 g (0.191 mole) triphenyl-phosphin are added and subsequently the suspension is heated up to simmering.

| Temperature: | Processing Time: | Observation: |
|---|---|---|
| 21° C. | | brown suspension |
| 25–70° C. | 4 h | orange suspension |
| 70–75° C. | 40 min | suspension becomes gradually darker and changes colors through brown to ruby-colored |
| 75° C. | | reaction occurred; a dark ruby-colored suspension has arisen (change point) |
| 75–79° C. | 25 min | ruby-colored suspension |
| 79–80° C. | | simmering starts; suspension is boiled for 1 h on reflux |

The suspension obtained is left to cool down over night without active cooling. On the following day cooling down to 20° C. by means of an ice bath takes place and subsequently filtering over a G3 frit. The product is rewashed on the frit with 405 ml of totally desalinated water and 235 ml isopropanol. Subsequently the frit cake is dried in the vacuum of membrane pumps. 35.82 g of ruby-colored fine crystalline solid are obtained.

The calculated yield amounts to 99.4%.

Example 4

4 g Rh (0.0389 mole) in form of an aqueous $RhCl_3$ solution with 23% Rh content is thinned with water to an Rh content of 10%.

490 ml isopropanol are mixed with the $RhCl_3$ solution. Then 50 g (0.191 mole) of triphenylphosphin is introduced into the flask and heated up to simmering in stages.

| Temperature: | Processing Time: | Observation: |
|---|---|---|
| 19° C. | | dark reddish brown solution with un-dissolved triphenylphosphin |
| 25–30° C. | 30 min | brown suspension |
| 30–74° C. | 3.25 h | orange suspension |
| 74–78° C. | 30 min | suspension becomes gradually darker and changes colors via brown to ruby-colored |
| 78° C. | | reaction occurred; a dark ruby-colored suspension has arisen (change point) |
| 78–79° C. | 15 min | ruby-colored suspension |
| 79–80° C. | | simmering starts; suspension is boiled for 1 h on reflux |

The suspension obtained is cooled down to 20° C. by means of an ice bath and subsequently filtered over a G3 frit. The product is rewashed on the frit with 235 ml isopropanol and 100 ml of petroleum benzine and dried in the vacuum of membrane pumps.

35.47 g of ruby-colored fine crystalline solid are obtained.

The calculated yield amounts to 98.5%.

Example 5

(Repeat of Example 4 but with 30% Less Solvent and Water)

343 ml isopropanol and 4 g Rh in form of an $RhCl_3$ solution with an Rh content of 10% are produced along with the triphenylphosphin are produced in the flask and similar to Example 4 heated to simmering in stages.

| Temperature: | Processing Time: | Observation: |
|---|---|---|
| 19° C. | | dark reddish brown solution with un-dissolved triphenylphosphin |
| 26–34° C. | 45 min | brown suspension |
| 34–68° C. | 3 h | orange suspension |
| 68–75° C. | 45 min | suspension becomes gradually darker and changes colors via brown to ruby-colored |
| 75° C. | | reaction occurred; a dark ruby-colored suspension has arisen (change point) |
| 75–79° C. | 15 min | ruby-colored suspension |
| 79–80° C. | | simmering starts; suspension is boiled for 1 h on reflux |

The suspension obtained is cooled down to 20° C. by means of an ice bath and subsequently filtered over a G3 frit. The product is rewashed on the frit with 235 ml isopropanol and 100 ml of petroleum benzine and dried in the vacuum of membrane pumps.

34.44 g of ruby-colored fine crystalline solid are obtained. The calculated yield amounts to 95%.

We claim:

1. Process for the manufacture of chlorotris(triphenylphosphine)-rhodium(I) by means of causing a reaction of $RhCl_3$ solution with triphenylphosphine, subsequently cooling down and filtering the crystalline precipitate obtained wherein the mixture of the reactants is treated in such a way that A is heated up to about 30° C. in an initial stage, B is heated up from 30 to about 75° C. in a second stage, C is maintained at 80 to 110° C.

2. Process for the manufacture of chlorotris(triphenylphosphine)-rhodium(I) by means of causing a reaction of $RhCl_3$ solution with triphenylphosphine, subsequently cooling down and filtering the crystalline precipitate obtained wherein a 30 to 40° C. warm mixture of reactants is treated in such a way that B is heated up from about 30° C. to 40° C. to about 75° C., C is maintained at 80 to 110° C.

3. Process for the manufacture of chlorotris(triphenylphosphine)-rhodium(I) wherein a solution of $RhCl_3$ is manufactured in water or an $RhCl_3$ solution is prepared from a recycling process, a solution, it necessary under cooling with a $C_2$–$C_5$ alcohol, is combined with alcohol, triphenylphosphine, if necessary under cooling, is added in excess, A in an initial stage the suspension obtained is heated up from about 5 to 20 to about 30° C., B further in a second stage heated up from about 30 to about 75° C., C is maintained at 80 to 110° C.

the solution obtained is cooled down, the crystals precipitated out are filtered, washed and subsequently dried.

4. Process for the manufacture of chlorotris(triphenylphosphine)-rhodium(I) wherein a solution of $RhCl_3$ is manufactured in water or an $RhCl_3$ solution is prepared from a recycling process, isopropanol is produced under a protective inert gas, the $RhCl_3$ solution is added triphenylphosphine is added in excess as an alcoholic solution or suspension A the mixture obtained is heated up from about 20 to about 30° C. in an initial stage, B further in a second stage is heated up from about 30 to about 75° C., C is boiled under reflux at 80 to 110° C.

the solution obtained is cooled down, the crystals precipitated out are filtered, washed with alcohol and/or water and/or petroleum ether and subsequently dried.

5. Process pursuant to claim 1, wherein the stages last: A, about ½ to 1 h; B, 1 to 4 h and C, about ½ to 1 h.

6. Process pursuant to claim 2, wherein the stages last: A, about ½ to 1 h; B, 1 to 4 h and C, about ½ to 1 h.

7. Process pursuant to claim 3, wherein the stages last: A, about ½ to 1 h; B, 1 to 4 h and C, about ½ to 1 h.

8. Process pursuant to claim 4, wherein the stages last: A, about ½ to 1 h; B, 1 to 4 h and C, about ½ to 1 h.

* * * * *

UNITED STATES PATENT AND TRADEMARK OFFICE
CERTIFICATE OF CORRECTION

| | |
|---|---|
| PATENT NO. | : 7,145,027 B2 |
| APPLICATION NO. | : 10/526912 |
| DATED | : December 5, 2006 |
| INVENTOR(S) | : Walter et al. |

Page 1 of 1

It is certified that error appears in the above-identified patent and that said Letters Patent is hereby corrected as shown below:

In the Claims

Column 6, Line 47, "it necessary" should read -- if necessary --

Signed and Sealed this
Eleventh Day of March, 2014

Michelle K. Lee
*Deputy Director of the United States Patent and Trademark Office*